US006323360B1

(12) United States Patent
Ruckenstein et al.

(10) Patent No.: US 6,323,360 B1
(45) Date of Patent: Nov. 27, 2001

(54) BREAKABLE CROSSLINKERS AN USE FOR PREPARATION OF POLYMERS USING SAME

(75) Inventors: Eli Ruckenstein; Hongmin Zhang, both of Amherst, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 09/712,324

(22) Filed: Nov. 14, 2000

Related U.S. Application Data
(60) Provisional application No. 60/166,590, filed on Nov. 19, 1999.

(51) Int. Cl.$^7$ .............................. C08F 22/10; C08L 33/08; C07C 69/34
(52) U.S. Cl. ...................... 560/199; 526/321; 526/323.1; 526/323.2; 526/329.6; 524/557; 524/561
(58) Field of Search .................................. 526/321, 323.1, 526/323.2, 329.6; 524/557, 561; 560/199

(56) References Cited

U.S. PATENT DOCUMENTS 2,889,192 * 6/1959 D'Adamo et al. .

FOREIGN PATENT DOCUMENTS 881 102 * 11/1961 (GB) .

* cited by examiner

Primary Examiner—James J. Seidleck
Assistant Examiner—Olga Asinovsky
(74) Attorney, Agent, or Firm—Hodgson Russ LLP

(57) ABSTRACT

The present invention discloses the synthesis of a novel crosslinker having the following structure:

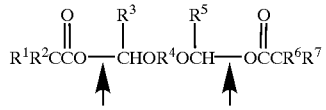

$R^1$ is $C(R^8)(R^9)$ wherein $(R^8)$ is H, or an alkyl group having 1–5 carbon atoms, and $(R^9)$ is H, or an alkyl group having 1–5 carbon atoms. $R^2$ is H, or an alkyl group having 1–5 carbon atoms. $R^3$ is H or an alkyl group having 1–5 carbon atoms. $R^4$ is an alkyl group having 1–5 carbon atoms. $R^5$ is H or an alkyl group having 1–5 carbon atoms. $R^6$ is H or an alkyl group having 1–5 carbon atoms. $R^7$ is $C(R^{10})(R^{11})$ wherein $(R^{10})$ is H, or an alkyl group having 1–5 carbon atoms, and $(R^{11})$ is H, or an alkyl group having 1–5 carbon atoms. The crosslinker is stable in a basic environment, but decomposable in an acidic environment.

17 Claims, 5 Drawing Sheets

BREAKABLE CROSSLINKERS AN USE FOR PREPARATION OF POLYMERS USING SAME

This application claims benefit of Provisional No. 60/166,590 filed Nov. 19, 1999.

FIELD OF INVENTION

The present invention relates generally to polymers. More particularly, the present invention provides novel crosslinkers for the preparation of star-shaped or branched polymers and polymer gels.

DISCUSSION OF RELATED ART

Divinyl cross-linking reagents (crosslinkers) have often been employed for the preparation of star-shaped (co) polymers. For example a linear living polymer has been prepared using a living polymerization technique, followed by the reaction of its living end with a small amount of divinyl compound. The addition of divinyl benzene (DVB) to an anionic living polystyrene [poly(St)] solution led to the formation of a star-shaped poly(St) with a central poly (DVB) gel. This method has also been extended to cationic, group transfer and metathesis polymerizations (all of these methods are well known to those skilled in the art) in which divinyl ethers, divinyl esters and norbornadiene dimers were used as crosslinkers, respectively. This synthetic technique is carried out by adding a bifunctional monomer to a completed living polymerization system.

SUMMARY OF THE INVENTION

The present invention discloses the synthesis of a novel crosslinker having the following structure:

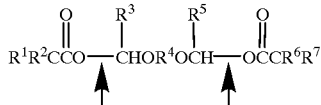

$R^1$ is $C(R^8)$ $(R^9)$ wherein $(R^8)$ is H, or an alkyl group having 1–5 carbon atoms, and $(R^9)$ is H, or an alkyl group having 1–5 carbon atoms. $R^2$ is H, or an alkyl group having 1–5 carbon atoms. $R^3$ is H or an alkyl group having 1–5 carbon atoms. $R^4$ is an alkyl group having 1–5 carbon atoms. $R^5$ is H or an alkyl group having 1–5 carbon atoms. $R^6$ is H or an alkyl group having 1–5 carbon atoms. $R^7$ is $C(R^{10})$ $(R^{11})$ wherein $(R^{10})$ is H, or an alkyl group having 1–5 carbon atoms, and $(R^{11})$ is H, or an alkyl group having 1–5 carbon atoms. The crosslinker is stable in a basic environment, but decomposable in an acidic environment.

DETAILED DESCRIPTION OF THE INVENTION

In the present invention, novel functional monomers, such as ethylene glycol di(1-methcryloyloxy)ethyl ether, EGDE, ethylene glycol di(1-acryloyloxy)ethyl ether, and the like, which are stable in a basic, but decomposable in an acidic, environment, were prepared. The preparation was done through the addition reaction between alkyl glycol divinyl ether and (meth)acrylic acid (MAA). These functional monomers can be used as the crosslinkers in the preparation of the star-shaped or branched polymers and polymer gels.

This novel crosslinker was used in the preparation of a star-shaped poly (methyl methacrylate) [poly(MMA)], a branched soluble poly(MMA) and a polymer gel. The star-shaped poly(MMA) was prepared using a standard method, known to those skilled in the art. Briefly, the living poly (MMA) was allowed to react with a small amount of EGDE to form a living block copolymer, which had a short segment of EGDE attached to the end of the polymer chain; the subsequent intermolecular reactions of the pendant vinyl groups of EGDE with the living ends of the polymer chains resulted in a star-shaped polymer with a central poly EGDE core. On the other hand, the simultaneous introduction of EGDE and MMA into a THF solution of an anionic initiator resulted in the formation of a branched soluble poly(MMA) or a polymer gel, depending on the amount of EGDE added, because the intermolecular cross-linking can occur as the polymerization proceeds. In contrast to the star-shaped polymers and polymer gels based on the conventional crosslinkers, such as ethylene glycol dimethacrylate, those prepared using EGDE could be easily broken by hydrolysis under mild acidic condition, generating linear polymers.

Figure 1:
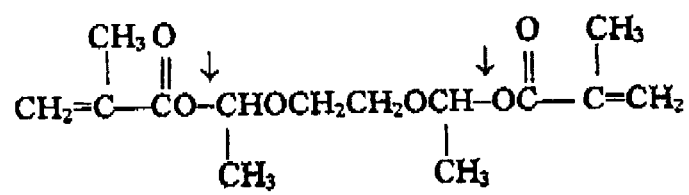
FIG. 1 is a representation of the molecular structure of ethylene glycol di(1-methacryloyloxy) ethyl ether, (hereinafter "EGDE"). The linkages indicated with arrows can be easily broken under acidic conditions.

In an acidic environment, the bonds of the EDGE, identified by arrows in FIG. 1, are broken. Compared to most polymer gels, the present gels exhibited different responses in the acid and basic media. In contrast to their swelling in a basic or neutral medium, clear solutions of linear polymers could be obtained when an acidic medium was employed. This may be useful for controlled drug release and is relevant to the environment protection.

The star-shaped and branched polymers and the polymer gels prepared based on these novel crosslinkers exhibit different properties in basic and acidic environments. As an illustration, described below is the synthesis of EGDE.

Materials

Tetrahydrofuran (THF) was dried with CaH₂ under reflux for at least 24 hours, distilled, and distilled again from a solution of 1,1-diphenylhexyllithium (DPHL) just before use. Toluene was washed with concentrated sulfuric acid and then with water, dried with $MgSO_4$, and distilled over $CaH_2$. Hexane was first dried and distilled over $CaH_2$ and then distilled from a solution of n-BuLi. Methyl methacrylate (MMA, Aldrich, 99%) was washed with a 10% aqueous sodium hydroxide solution and then with water, dried overnight with $MgSO_4$ and distilled twice over $CaH_2$ prior to polymerization. 1,1-Diphenylethylene (DPE, Aldrich, 97%) was distilled over $CaH_2$ and then distilled in the presence of DPHL under reduced pressure. Lithium chloride (Aldrich, 99.99%) was dried at 120° C. for 24 h and dissolved in THF. n-BuLi (Aldrich, 1.6 M solution in hexane) was diluted with purified hexane.

Synthesis of EDGE

EGDE was prepared through the addition reaction between ethylene glycol divinyl ether; Aldrich, 97%) and methacrylic acid (MAA; Aldrich, 99.8%) in the presence of a trace amount of the inhibitor 4-tert-butylcatechol, under the protection of nitrogen, with magnetic stirring. In a 250 mL round-bottom flask equipped with a condenser and a magnetic stirrer, 25.0 g (0.21 mol) EGDE and a small amount of 4-tert-butylcatechol were introduced. After 4-tert-butylcatechol had dissolved and the temperature was raised to 70° C., MAA (36.5 g, 0.42 mol) was dropwise added with a syringe in about 20 minutes. The reaction was allowed to last 6.0 hours and the crude product was distilled under high vacuum. The monomer was dissolved in purified toluene (30 v/v%) and this solution was purified with $CaH_2$ and filtered through a tube filter with reduced ends in a completely sealed apparatus. This purification process was repeated prior to polymerization and the toluene solution was directly used. The high purity of EGDE was confirmed by $^1H$ NMR ($CDCL^3$): $\delta1.42$ (d, 6H, $OCH(CH_3)O$), 1.95 (s, 6H, $\alpha$-$CH_3$), 3.60–3.83 (m, 4H, $OCH_2CH_2O$), 5.59 and 6.15 (2s, 4H, $CH_2$=), 6.00 (m, $2H,OCH(CH_3)O$).

Polymerization

The anionic polymerization was carried out in THF, in a round-bottom glass flask, under an over pressure of argon, with magnetic stirring, at a selected temperature, in the presence of LiCl. After THF, DPE and a THF solution of LiCl were added with dry syringes, the flask was cooled to −40° C. and n-BuLi (in hexane) was added. The deep red color of DPHL appeared, and the reaction between n-BuLi and DPE was allowed to continue for 15 min. For the preparation of star-shaped polymer, prechilled MMA was first added and the polymerization was allowed to last 50 minutes at −78° C. Then, the system was warmed to −50° C. and a toluene solution of EGDE was added. After the cross-linking reaction lasted 3 hours, the system was quenched with a small amount of methanol and the polymer was precipitated by pouring the polymerization solution into hexane. Then, the polymer was reprecipitated in ethanol from a benzene solution and vacuum-dried overnight.

In the cases of branched poly(MMA) and polymer gels, a prechilled mixture of MMA and a toluene solution of EGDE was added to the initiator solution and the reaction was allowed to last 2 hours at −50° C. The branched poly(MMA) was purified in a way similar to that used for the star-shaped polymer. To purify the polymer gel, hexane containing a small amount of methanol was added and after 3 hours, it was dried under reduced pressure at 50° C. for 24 hours.

Hydrolysis of the Star-Shaped Polymer, the Branched Polymer and the Polymer Gel

The hydrolysis of star-shaped or branched poly(MMA) was carried out in acetone, in the presence of a small amount of an aqueous solution of HCl, at room temperature, with magnetic stirring. For instance, 1.2 grams vacuum-dried star-shaped poly(MMA) (SSP-3 in Table 1) was redissolved in 30 mL acetone, to which 1.0 mL HCl aqueous solution (6.0 M) was added. After 20 minutes, this mixture was poured into hexane to precipitate the polymer. The polymer thus obtained was washed with hexane and vacuum-dried at 40° C. for 24 hours.

The hydrolysis of the polymer gel was performed either in THF or in acetone, using either acetic acid or an aqueous solution of HCl. For comparison, the reaction was also carried out under basic conditions in the presence of sodium hydroxide. In 30 mL solvent, 1.0 gram of polymer gel and a certain amount of acid were added. The corresponding time to form a completely transparent solution was recorded (Table 3). The hydrolyzed polymer was purified as described above.

Measurements $^1H$ NMR spectra were recorded in $CDCl_3$ or $CD_3OD$ on an INOVA-400 spectrometer. $M_n$ and $M_w/M_n$ of the polymer were determined by gel permeation chromatography (GPC) on the basis of a polystyrene calibration curve. The GPC measurements were carried out using THF as solvent, at 30° C., with a 1.0 mL/min flow rate and a 1.0 cm/min chart speed. Three polystyrene gel columns (Waters, 7.8×300 mm; one HR 5E, Part No. 44228, one Linear, Part No. 10681 and one HR 4E, Part No. 44240) were used, which were connected to a Waters 515 precision pump. The FT-IR spectra were recorded on a Perkin-Elmer 1760-X spectrometer using KBr tablets.

Preparation of Star-Shaped Poly(MMA)

The preparation of star-shaped poly(MMA) was carried out in a two-step process, namely, the living anionic polymerization of MMA and the reaction of the resulting living polymer with EGDE. In the first step, the initiator DPHL was prepared in situ before the monomer addition, via the reaction of n-BuLi with DPE ($[DPE]/[n-BuLi]_0=1.2$), in THF, at −40° C., in the presence of LiCl ($[LiCl]/[n-BuLi]_0=1.2$), for about 15 min, The anionic polymerization was induced by adding prechilled MMA ($[MMA]_0=0.667$ M) to the above initiator solution ($[DPHL]_0=16.7$ mM) and the reaction was allowed to last 50 minutes at −78° C. The molecular weight (MN) of the obtained poly(MMA) was in good agreement with the designed value ($M_k=4230$) and the molecular weight distribution (MWD) was very narrow ($M_w/M_n \leq 1.06$. see FIGS. 2A and 3A).

Figure 2:
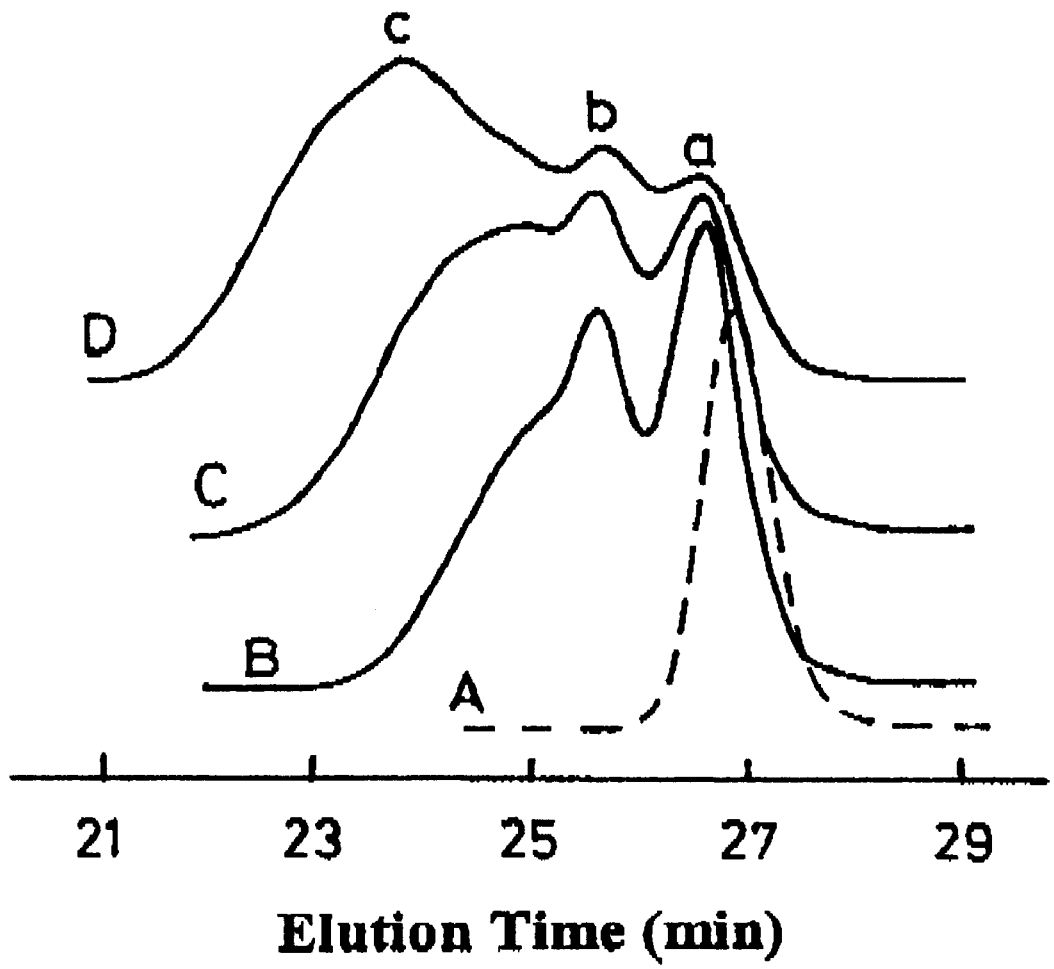
FIG. 2 is a representation of GPC traces of star-shaped polymers and their precursor. A: Living linear polymethyl methacrylate ("poly(MMA)") ($M_n$=4140, $M_w/M_n$=1.06). B, C, and D: Star shaped poly(MMA)s (Table 1; SSP-1, C:SSP-2, D:SSP-3) prepared by adding EGDE to the above living poly(MMA) solution, for [EGDE]₀/[DPHL]₀ ratios of 3, 5 and 8 respectively.

In the second step, the living poly(MMA) was allowed to react with EGDE for $[EGDE]_0/[DPHL]_0$ ratios of 3, 5 or 8. The cross-linking reaction was allowed to last 3 h at −50° C. The reaction proceeded quantitatively and produced a completely soluble product. As shown in FIG. 2, the resulting polymers possess broad MWDS, and the star-shaped polymers (peak c) are accompanied by low molecular weight polymers (peaks a and b). Peak a corresponds to a higher molecular weight ($M_n \approx 5600$) than that of its living poly (MMA) precursor ($M_n=4140$) and this can be attributed to a block copolymer of MMA and EGDE. The $M_n$ corresponding to peak b is about 14000 and this fraction is most likely a star-shaped polymer with a low arm number (about 3). The presence of peaks a and b indicates that the crosslinking reaction was incomplete. As the amount of EGDE increased, the a and b fractions decreased, being incorporated into the star-shaped polymer with high molecular weight.

It has been reported that the molecular structure of the crosslinker greatly affects the yield of the star-shaped polymer For instance, when the cationically prepared living polymer of isobutyl vinyl ether (IBVE) was reacted with bisphenol A derived divinyl ether, a star-shaped poly(IBVE) was obtained with high selectivity. However, when this crosslinker with rigid aromatic units was replaced with a flexible divinyl ether, such as di(ethylene glycol) divinyl ether, the resulting star-shaped polymer was accompanied by low molecular weight polymers. Similarly, the crosslinker EGDE also possesses a flexible spacer. After the cross linking proceeds to a certain extent, the flexibility of the crosslinker makes its pendant double bond less exposed and hence less accessible for further reactions with the incoming living chains. The increase of the amount of EGDE will generate a larger core, thus providing a larger number of accessible vinyl groups. For this reason, the fraction of star-shaped polymer will increase (FIG. 2D).

Figure 3:
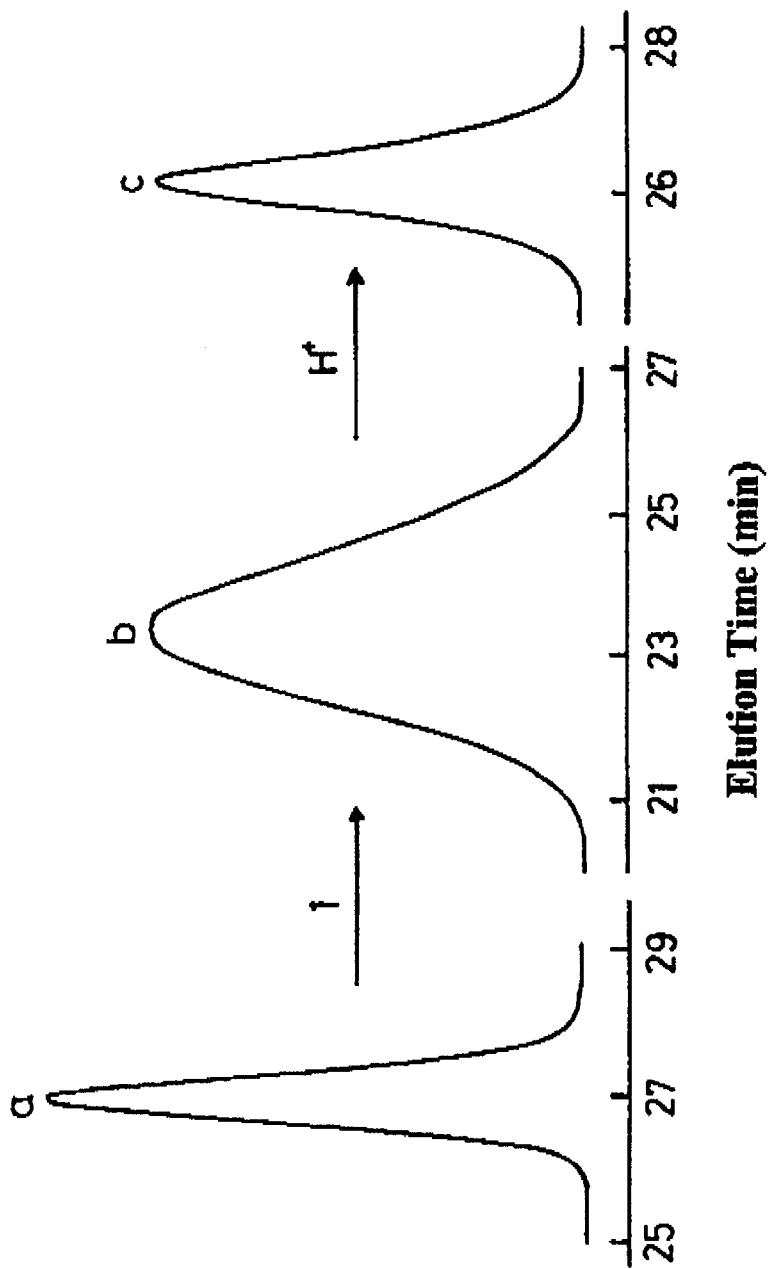
FIG. 3 is a representation of GPC traces of reprecipitated star-shaped poly(MMA) from SSP-3 (peak b, $M_n$=34000, $M_w/M_n$=1.55), its living poly(MMA) precursor (peak a, $M_n$=4180, $M_w/M_n$=$M_n$=4140, $M_w/M_n$=1.05) and its hydrolyzed polymer (peak c, $M_n$=6500, $M_w/M_n$=1.15).

Because of the presence of the low molecular weight fractions (peaks a and b), the average molecular weight of the resulting polymer was low. For instance, the $M_n$ of SSP-3 in Table 1 is 15300 and, according to this value, the calculated arm number of the star-shaped polymer is small (3.6). However, this is not the real value, because the star-shaped polymer is not pure. In order to obtain a pure star-shaped polymer, reprecipitation was carried out to remove the low molecular weight fractions. For instance, 2.0 g SSP-3 (Table 1) was redissolved in 60 mL benzene and this solution was poured into 400 mL ethanol. As shown in FIG. 3$b$, the reprecipitated polymer exhibits a single GPC peak. According to the molecular weight of the reprecipitated SSP-3 ($M_n$=34000), the calculated arm number of the star-shaped polymer is about 8, which is much higher than that before reprecipitation.

Preparation of the Branched Soluble Poly(MMA) and Polymer Gel

Great attention was accorded to polymer gels, because of their applications in various fields, such as medicine, nutritive and petrochemical industries, agriculture, biotechnology, etc. The synthesis of pH-sensitive polymer gels and their applications in drug delivery have been widely investigated. Because of the presence of ionizable groups in this kind of polymer gels, swelling or deswelling can occur along with pH changes. However, the pH change does not affect or change their chemical composition and molecular structure. In contrast to those polymer gels, a different polymer gel was prepared using the crosslinker EGDE, because this insoluble gel can be changed to soluble linear polymers by changing the pH.

In contrast to the preparation of the star-shaped poly (MMA), MMA and a toluene solution of EGDE were introduced into a THF solution of the initiator (DPHL) at the same time. The reaction was allowed to last 2 h at –50° C. Because both MMA and the crosslinker EGDE participate simultaneously in the polymerization, a polymer gel could be obtained through the intermolecular cross-linking reaction.

For a fixed initial concentration of MMA ([MMA]$_0$=0.588 M), the characteristics of a polymer gel depend on the concentrations of both the initiator and the crosslinker EGDE. Low [DPHL]$_0$ and high [EGDE]$_0$ are beneficial for the cross-linking reaction. As shown in Table 2, when [DPHL]$_0$=14.7 mN and [EGDE]$_0$=29.4 mM (BP-1), cross-linking occurred to some extent, but the polymer remained soluble. Even when the concentration of EGDE was doubled to increase the number of cross-linking points (BP-2), or the concentration of DPHL was reduced to half to increase the molecular weight (BP-3), the polymers still remained soluble and the magnetic stirring was still possible in spite of a very high viscosity. The resulting polymers (BP-2 and -3) have higher molecular weights and broader MWDs than BP-1 (Table 2). Consequently, when the concentration of the crosslinker EGDE was sufficiently low and/or the initiator concentration was sufficiently high, the resulting products were soluble branched polymers, probably accompanied by some looped and cyclic polymer chains. For this reason, the MWDs were broad. However, when [EGDE]$_0$ was taken twice as large and [DPHL]$_0$ was simultaneously reduced to half that for BP-1, the magnetic stirring became impossible only after a few minutes upon the addition of MMA and EGDE, and a polymer gel was generated (PG-1 in Table 2). The further reduction of [DPHL]$_0$ (PG2 in Table 2) or the homopolymerization of EGDE [DPHL]$_0$ =7.4 mM, [EGDE]$_0$=0.400 M) generated polymer gels easily.

Hydrolysis of Star-Shaped Polymers, Branched Polymers and Polymer Gels

The hydrolysis of the star-shaped or branched polymer was carried out in acetone, at room temperature, in the presence of a small amount of hydrochloric acid (see Experimental Section). FIG. 3$b$ presents the GPD chromatogram of a reprecipitated star-shaped poly(MMA) (peak b), which has, obviously, a larger molecular weight and a broader MWD ($M_n$=34000, $M_w/M_n$=1.55) than its living linear poly (MMA) precursor (peak a, $M_n$=4180, $M_w/M_n$=1.05). The hydrolysis of this star-shaped polymer resulted in the formation of a polymer with a lower molecular weight and a narrower MWD (peak c, $M_n$=6500, $M_w/M_n$=1.15). This hydrolyzed product is most likely a block copolymer consisting of poly(MMA) and poly(methacrylic acid) [poly (MAA)] segments as described below and for this reason, its molecular weight is larger than that of the linear poly(MMA) precursor (peak a).

Figure 4:
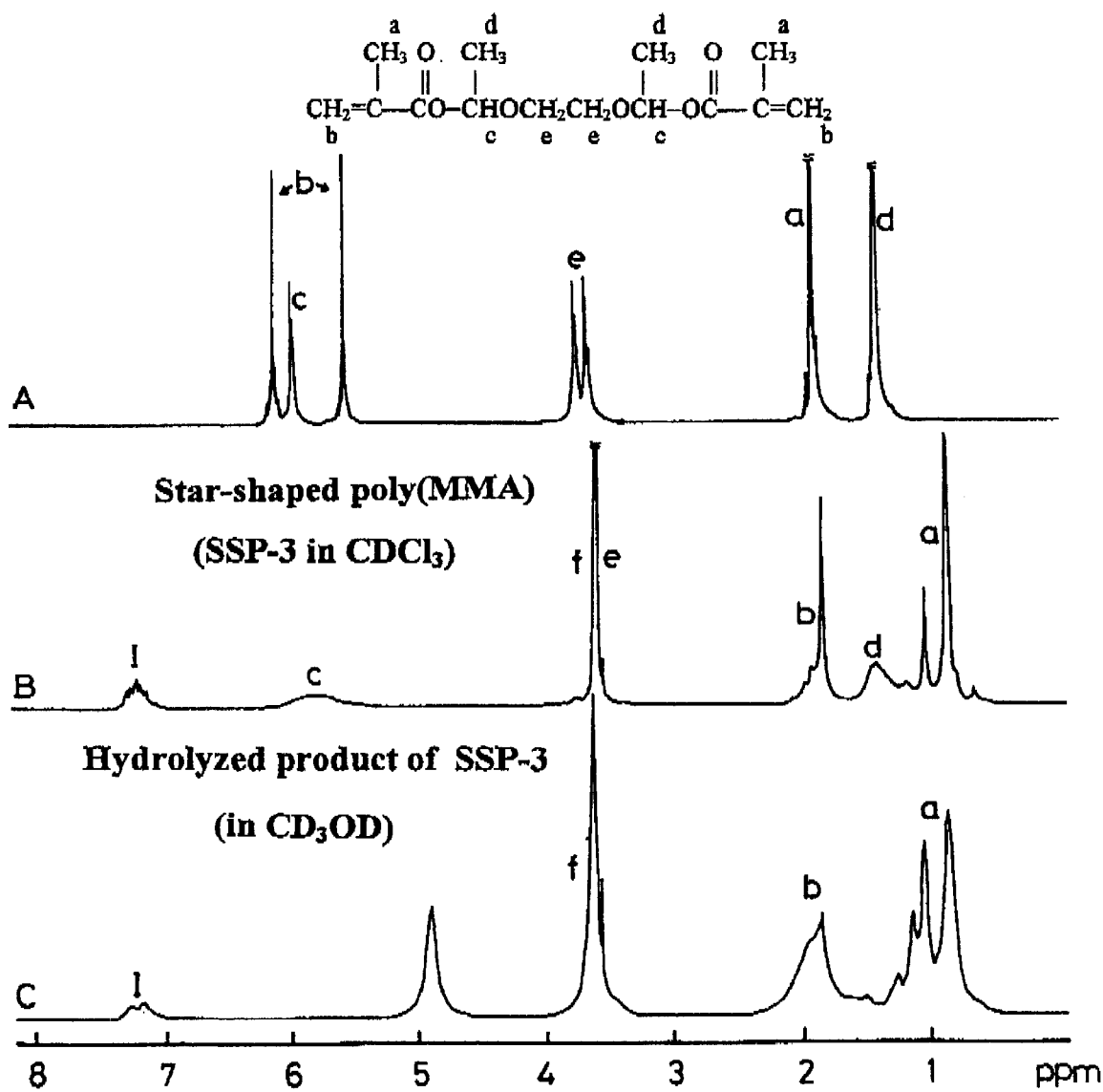
FIG. 4 is a representation of the $^1$H NMR spectra of EGDE (A; in CDCl₃), star-shaped poly(MMA) (B;SSP-3 in CDCl₃; see Table 1 and FIG. 3b) and its hydrolyzed polymer (C; in CD₃OD, see Table I and FIG. 3c). Absorptions due to poly(MMA) segment: peak a, α-CH₃; peak b, —CH₂— in the main chain; peak f, —OCH₃ in the side chain; I: C₆H₅ of the initiator (DPHL).

In order to identify the cleavage point, the hydrolyzed product was characterized by $^1$H NMR and FT-IR. FIG. 4 depicts the $^1$H NMR spectra of the star-shaped polymer (B) and its hydrolyzed product (C). For comparison, the $^1$H NMR spectrum of EGDE is also included in FIG. 4A. Comparing Figures A and B, one can observe that the peaks a and b, corresponding to the $\alpha$-methyl and H$_2$C=of EGDE, shifted to 0.8~1.1 and 1.8~2.1 ppm after cross-linking and overlapped with the absorptions of the $\alpha$-CH$_3$ (B-a) and —CH$_2$(B-b) belonging to poly(MMA). On the other hand, the peaks c, d and e of the side chain of EGDE did not change and could be detected in the spectrum of the star-shaped polymer (B). However, these absorptions disappeared completely in the spectrum of the hydrolyzed product (C), indicating that the ester groups of the crosslinker EGDE were eliminated to yield the poly(MAA) segment. This result was also confirmed by FT-IR; the hydrolyzed polymer exhibits a broad absorption (2500~3800 cm$^{-1}$) corresponding to the carboxyl group of poly(MAA) segment. On the other hand, the absorption due to the ester group (—OCH$_3$) of poly(MMA) segment is still present quantitatively in the $^1$H NMR spectrum of the hydrolyzed polymer (peak f in FIG. 4C). The above results indicate that the hydrolysis reaction fractured selectively the cross-linking points to generate linear block copolymers of MMA and MAA.

Figure 5:
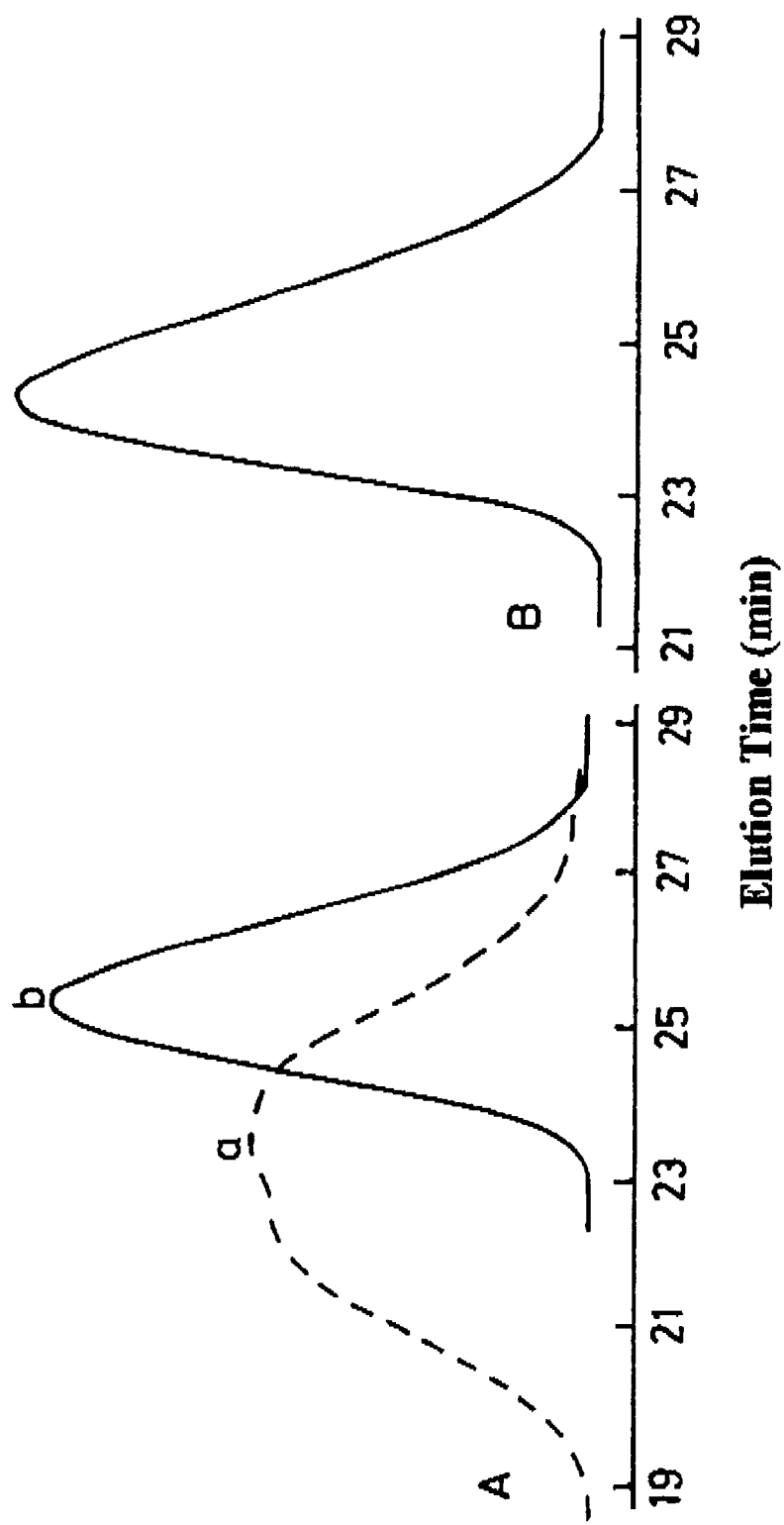
FIG. 5 is a representation of GPC traces of the hydrolyzed polymers from the branched soluble poly(MMA) (A) and polymer gel (B). A-a: $M_n$=9790, $M_w/M_n$=1.46. B:hydrolyzed polymer ($M_n$=12900, $M_w/M_n$=1.63) from polymer gel, PG-1 (Table 2).

Similarly, the hydrolysis of the branched soluble polymer can also generate a linear polymer via the same mechanism. As shown in FIG. 5A, the hydrolyzed polymer possesses a lower molecular weight and a narrower MWD (Peak A-b, $M_n$=9790, $M_w/M_n$=1.46) than its precursor polymer (peak A-a, BP-2 in Table 2, $M_n$=33000, $M_w/M_n$=2.43). Its Ft-IR spectrum also confirmed the presence of the carboxyl groups of poly(MAA) units (2500~3800 cm$^{-1}$). However, the hydrolyzed product is a random copolymer of MMA and MAA, because MMA and the crosslinker EGDE participated in the polymerization simultaneously.

The hydrolysis of the polymer gel is more interesting, because this is a process that changes the insoluble polymer to a soluble linear polymer. As shown in Table 3, the response of the polymer gel depends mainly on the acidity of the medium and to some extent on the solvent employed. In a basic (no.1, NaOH.) or a neutral (no.2, $H_2O$) environment, the polymer gel is swollen, but the cross-linking points are not destroyed. When a weak acid, acetic acid, was used (no. 3 and 4), the polymer gel transformed after a long time (24–36 h) into small particles which dispersed in the medium. However, in the presence of a trace amount of hydrochloric acid (no. 5 and 6, [HC1]=0.015 M), a transparent solution was obtained in less than 20 min and this time got shorter with increasing acid concentration (no. 7–9). When [HC1]=0.2 M, a completely transparent polymer solution could be obtained in 5 min (no. 9). One can also note from Table 3 that the change occurred easier in acetone than in THF, because the former is a better solvent for both poly(MMA) and poly(MAA) segments. As for the branched soluble poly(MMA), the hydrolyzed product of the poly (MMA) gel is also a linear random copolymer of MMA and MAA. Its GPC chromatogram exhibits a single peak (FIG. 5B) and the presence of carboxyl groups in the MAA units was confirmed by FT-IR (2500~3800 $cm^{-1}$). In addition, the polymer gel prepared via the homopolymerization of EGDE could also be hydrolyzed to a linear polymer [poly(MAA)] in methanol in the presence of HC1 ([HC1]=0.2 M) in 20 min.

The hydrolyzed products of star-shaped polymers, branched polymers and polymer gels possess quite different solubilities compared to their precursors (Table 4). The hydrolyzed star-shaped polymers (h-SSP-1, h-SSP-2 and h-SSP-3) are soluble in methanol, but insoluble in benzene, due to the presence of the hydrophilic poly(MA-A) block. On the other hand, the polymer gel is insoluble in all solvents before hydrolysis. However, its hydrolyzed product is soluble in acetone, THF, 1,4-dioxane and N,N-dimethylformamide (DMF), but insoluble in benzene and only wetted by methanol due to the presence of the random MAA units.

TABLE 1

Preparation of Star-Shaped Poly(MMA) (SSP)[a]

| no. | $[EGDE]_0/$ $[DPHL]_0$ | star[b] $M_n{}^d$ | $M_w/M_n{}^d$ | $M_n$ (calcd) | hydrolyzed product[c] $M_n$ (obsd)[d] | $M_w/M_n{}^d$ |
|---|---|---|---|---|---|---|
| SSP-1 | 3 | 8420 | 1.42 | 4760 | 4840 | 1.12 |
| SSP-2 | 5 | 10200 | 1.72 | 5100 | 5460 | 1.12 |
| SSP-3 | 8 | 15300 | 2.24 | 5620 | 6500 | 1.15 |

[a]The initiator, DPHL, was prepared via the reaction of n-BuLi with DEP ([DPEI/(n-BuLi]$_0$ = 1.2), in THF, at −40° C., in the presence of LiCl ([LiCl]/[n-BuLi]$_0$ = 1.2), for 15 minutes.
The anionic polymerization of MMA was performed by adding prechilled MMA ([MMA]$_0$ = 0.667M) to the above initiator solution ([DPHL]$_0$ = 16.7 mM) and the reaction was allowed to last 50 minutes at −78° C. Then, the system was warmed to −50° C. and a toluene solution of 1 was added. This cross-linking reaction was allowed to last an additional 3 hours.
[b]Before reprecipitation.
[c]The hydrolysis was carried out after the reprecipitation.
[d]Determined by GPC.

TABLE 2

Preparation of the Branched Soluble Poly(MMA) (BP) and Polymer Gel (PG)[a]

| no. | $[DPHL]_0$ MM | $[1]_0$ mM | stirring | before hydrolysis $M_n{}^b$ | $M_w/M_n{}^b$ | after hydrolysis $M_n{}^b$ | $M_w/M_n{}^b$ |
|---|---|---|---|---|---|---|---|
| BP-1 | 14.7 | 29.4 | OK | 14100 | 1.69 | 9440 | 1.40 |
| BP-2 | 14.7 | 58.8 | OK | 33000 | 2.43 | 9790 | 1.46 |
| BP-3 | 7.4 | 29.4 | OK | 49100 | 3.10 | 15100 | 1.57 |
| PG-1 | 7.4 | 58.8 | NO | gel | | 12900 | 1.63 |
| PG-2 | 5.9 | 58.8 | NO | gel | | 15900 | 1.74 |

[a]The initiator, DPHL, was prepared via the reaction of n-BuLi with DPE ([DPE]/[n-BuLi]$_0$ = 1.2), in THF, at −40° C., in the presence of LiCl ([LiCl]/(n-BuLi]$_0$ = 1.2), for 15 minutes.
The polymerization was induced by adding a prechilled mixture of MMA ([MMA]$_0$ = 0.588M) and a toluene solution of EGDE to the above initiator system and the reaction was allowed to last 2 hours at −50° C.
[b]Determined by GPC.

TABLE 3

Response of the Poly(MMA) Gel[a]

| no. | solvent | catalyst/M | time | response |
|---|---|---|---|---|
| 1. | acetone | Nah./0.42 | 24 h | swelling |
| 2. | acetone | $H_2O$/0.95 | 24 h | swelling |
| 3. | THF | AA[b]/0.26 | 36 h | peptization |
| 4. | acetone | AA[b]/0.26 | 24 h | peptization |
| 5. | THF | HCl/0.015 | 20 min | clear solution |
| 6. | acetone | HCl/0.015 | 15 min | clear solution |
| 7. | acetone | HCl/0.05 | 10 min | clear solution |
| 8. | THF | HCl/0.2 | 10 min | clear solution |
| 9. | acetone | HCl/0.2 | 5 min | clear solution |

[a]The reaction was carried out at 20° C. with magnetic stirring (solvent: 30 mL; polymer gel: 1.0 g).
[b]Acetic acid.

TABLE 4

Solubility before and after Hydrolysis

| | $CH_3OH$ | acetone | THF | dioxane | DMF | $CHCL_3$ | benzene |
|---|---|---|---|---|---|---|---|
| SSP-1 | I | S | S | S | S | S | S |
| h-SSP-1 | D | S | S | D | S | S | I |
| SSP-2 | I | S | S | S | S | S | S |
| h-SSP-2 | S | S | S | D | S | C | I |
| SSP-3 | I | S | S | D | S | S | D |
| h-SSP-3 | S | S | D | D | S | C | I |
| BP-1 | I | S | S | D | S | S | S |
| h-BP-1 | W | S | S | S | S | S | C |
| BP-2 | I | S | D | D | D | S | D |
| h-BP-2 | W | S | S | D | S | C | I |
| BP-3 | I | S | S | D | S | S | D |
| h-BP-3 | W | S | S | D | S | D | C |
| GP-1 | I | I | I | I | I | I | I |
| h-GP-1 | W | S | S | D | S | W | I |
| GP-2 | I | I | I | I | I | I | I |
| g-GP-2 | W | S | S | D | S | W | I |

[a]The experiment was carried out at room temperature. The amounts of polymer (or polymer gel) and solvent were 0.03 g and 1.0 mL, respectively. S: Soluble; D: Dissolved slowly; W: Wetting; C: Cloudy; I: Insoluble. h-: Hydrolyzed product from the corresponding polymer or polymer gel.

The foregoing description of the specific embodiments is for the purpose of illustration and is not to be construed as restrictive. From the teachings of the present invention, those skilled in the art will recognize that the device may be modified without departing from the spirit of the invention.

We claim:

1. A monomer compound comprising the following structure:

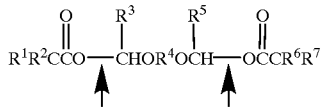

wherein $R^1$ is $C(R^8)(R^9)$ wherein $(R^8)$ is H, or an alkyl group having 1–5 carbon atoms, and $(R^9)$ is H, or an alkyl group having 1–5 carbon atoms;

wherein $R^2$ is H, or an alkyl group having 1–5 carbon atoms;

wherein $R^3$ is H or an alkyl group having 1–5 carbon atoms;

wherein $R^4$ is an alkyl group having 1–5 carbon atoms;

wherein $R^5$ is H or an alkyl group having 1–5 carbon atoms;

wherein $R^6$ is H or an alkyl group having 1–5 carbon atoms;

wherein $R^7$ is $C(R^{10})(R^{11})$ wherein $(R^{10})$ is H, or an alkyl group having 1–5 carbon atoms, and $(R^{11})$ is H, or an alkyl group having 1–5 carbon atoms; and wherein the monomer compound is stable in a basic environment, but decomposable in an acidic environment.

2. The monomer compound of claim 1 wherein the monomer compound is ethylene glycol di(1-methacryloyloxy)ethyl ether.

3. The monomer compound of claim 1 wherein the monomer compound is ethylene glycol di(1-acryloyloxy)ethyl ether.

4. The monomer compound of claim 1 wherein the monomer compound, while in an acidic environment, breaks at the bonds indicated by the arrows.

5. A polymer material comprising at least one monomer compound having the following structure:

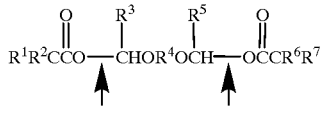

wherein $R^1$ is $C(R^8)(R^9)$ wherein $(R^8)$ is H, or an alkyl group having 1–5 carbon atoms, and $(R^9)$ is H, or an alkyl group having 1–5 carbon atoms;

wherein $R^2$ is H, or an alkyl group having 1–5 carbon atoms;

wherein $R^3$ is H or an alkyl group having 1–5 carbon atoms;

wherein $R^4$ is an alkyl group having 1–5 carbon atoms;

wherein $R^5$ is H or an alkyl group having 1–5 carbon atoms;

wherein $R^6$ is H or an alkyl group having 1–5 carbon atoms;

wherein $R^7$ is $C(R^{10})(R^{11})$ wherein $(R^{10})$ is H, or an alkyl group having 1–5 carbon atoms, and $(R^{11})$ is H, or an alkyl group having 1–5 carbon atoms; and wherein the at least one monomer compound is stable in a basic environment, but decomposable in an acidic environment.

6. The polymeric material of claim 5 wherein the at least one monomer compound is ethylene glycol di(1-methacryloyloxy)ethyl ether.

7. The polymeric material of claim 5 wherein the at least one monomer compound is ethylene glycol di(1-acryloyloxy)ethyl ether.

8. The polymeric material of claim 5 wherein the at least one monomer compound, while in an acidic environment, breaks at the bonds indicated by the arrows.

9. The polymeric material of claim 5 further comprising a second monomer.

10. The polymeric material of claim 9 wherein the second monomer is selected from the group consisting of methyl methacrylate, isobutyl vinyl ether, methacrylic acid and mixtures thereof.

11. The polymeric material of claim 5 wherein the polymeric material is a star-shaped polymer.

12. The polymeric material of claim 5 wherein the polymeric material is a branched polymer.

13. The polymeric material of claim 5 wherein the polymeric material is a polymer gel.

14. The polymeric material of claim 5 wherein the polymeric material is used within a mammal.

15. The polymeric material of claim 5 wherein the polymeric material is used decrease the pollution in the environment.

16. The polymeric material of claim 5 wherein the polymeric material when hydrolyzed is soluble.

17. A method of forming a polymeric material comprising the steps of:

mixing a first monomer with a second monomer having the following structure:

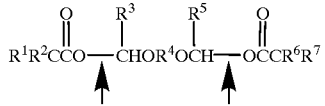

wherein $R^1$ is $C(R^8)(R^9)$ wherein $(R^8)$ is H, or an alkyl group having 1–5 carbon atoms, and $(R^9)$ is H, or an alkyl group having 1–5 carbon atoms;

wherein $R^2$ is H, or an alkyl group having 1–5 carbon atoms;

wherein $R^3$ is H or an alkyl group having 1–5 carbon atoms;

wherein $R^4$ is an alkyl group having 1–5 carbon atoms;

wherein $R^5$ is H or an alkyl group having 1–5 carbon atoms;

wherein $R^6$ is H or an alkyl group having 1–5 carbon atoms;

wherein $R^7$ is $C(R^{10})(R^{11})$ wherein $(R^{10})$ is H, or an alkyl group having 1–5 carbon atoms, and $(R^{11})$ is H, or an alkyl group having 1–5 carbon atoms; and wherein the second monomer compound is stable in a basic environment, but decomposable in an acidic environment; and forming a polymer design selected from the group consisting of a star-shaped polymer, a branched polymer, or a gel polymer.

* * * * *

UNITED STATES PATENT AND TRADEMARK OFFICE
CERTIFICATE OF CORRECTION

PATENT NO. : 6,323,360 B1
DATED : November 27, 2001
INVENTOR(S) : Eli Ruckenstein et al.

It is certified that error appears in the above-identified patent and that said Letters Patent is hereby corrected as shown below:

<u>Title page, Item [54] and Column 1, line 1,</u>
Title, please change "AN" to -- AND --.

Signed and Sealed this

Twentieth Day of August, 2002

Attest:

Attesting Officer

JAMES E. ROGAN
*Director of the United States Patent and Trademark Office*